United States Patent
Bardonaro, Jr.

(10) Patent No.: US 11,684,688 B2
(45) Date of Patent: Jun. 27, 2023

(54) APPARATUS THAT ATTACHES TO MOBILE ELECTRONIC DEVICES AND DISTRIBUTES SANITIZER/DISINFECTANTS

(71) Applicant: Frank Gary Bardonaro, Jr., Union, KY (US)

(72) Inventor: Frank Gary Bardonaro, Jr., Union, KY (US)

(*) Notice: Subject to any disclaimer, the term of this patent is extended or adjusted under 35 U.S.C. 154(b) by 484 days.

(21) Appl. No.: 16/846,988

(22) Filed: Apr. 13, 2020

(65) Prior Publication Data
US 2021/0316028 A1    Oct. 14, 2021

(51) Int. Cl.
*A61L 2/26* (2006.01)
*A61L 2/18* (2006.01)

(52) U.S. Cl.
CPC ...... *A61L 2/26* (2013.01); *A61L 2/18* (2013.01); *A61L 2202/15* (2013.01); *A61L 2202/16* (2013.01); *A61L 2202/181* (2013.01)

(58) Field of Classification Search
None
See application file for complete search history.

(56) References Cited

FOREIGN PATENT DOCUMENTS

FR    3029077 A1 *   6/2016
FR    3042689 A1 *   4/2017

OTHER PUBLICATIONS

Charon et al. FR3029077A1-translated document (Year: 2016).*
Chauvin et al. FR3042689A1-translated document (Year: 2017).*
Charon, J. FR3029077A1-translated document (Year: 2016).*

* cited by examiner

*Primary Examiner* — Jelitza M Perez
(74) *Attorney, Agent, or Firm* — Dunlap Bennett & Ladwig, PLLC

(57) ABSTRACT

A piggybacking apparatus for mobile devices is provided. The piggybacking apparatus may be dimensioned and adapted to removably attach to the surface area of a mobile electronic device, such as a smart phone, in a generally coextensive manner. The piggybacking apparatus may provide a pouch for retrievably storing fluid and semifluid product that a user wants handy when they are handling the mobile electronic device, Through a conduit the user may urge the product from the pouch when and where desired. The piggybacking apparatus may also provide attachment points along a periphery thereof for operatively associating with the mobile electronic device in the coextensive manner, or alternatively to a case of the mobile electronic device, or even in between the two.

8 Claims, 3 Drawing Sheets

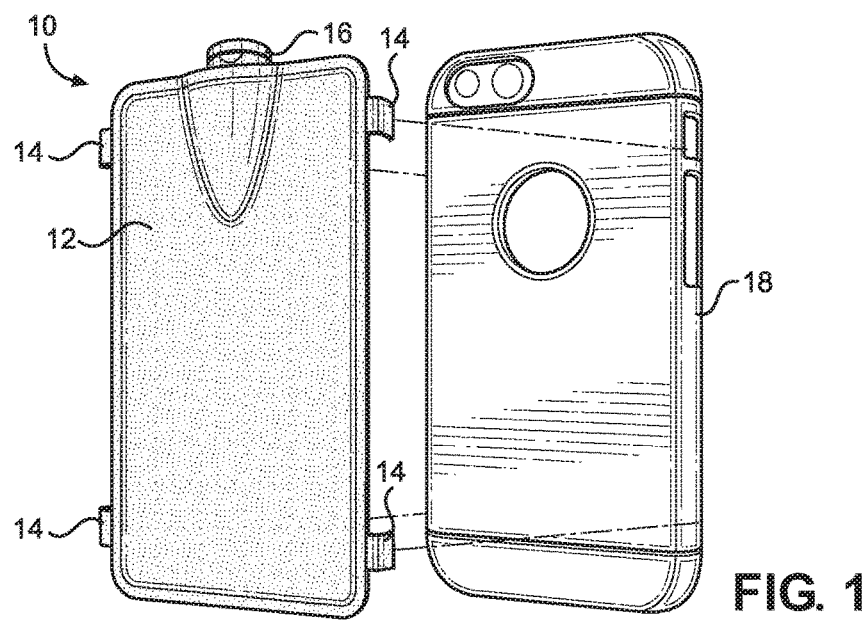
FIG. 1
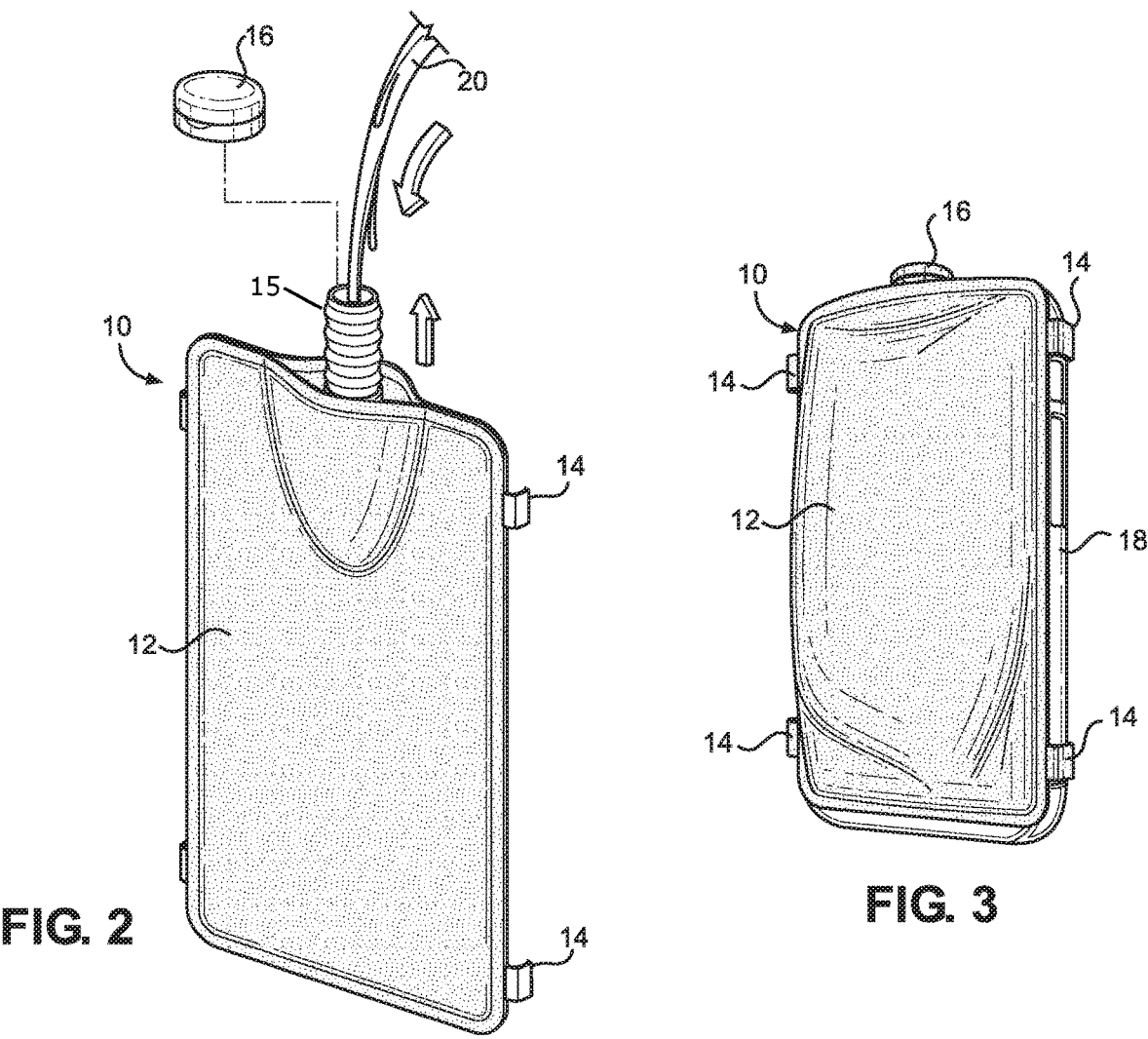
FIG. 2
FIG. 3

APPARATUS THAT ATTACHES TO MOBILE ELECTRONIC DEVICES AND DISTRIBUTES SANITIZER/DISINFECTANTS

BACKGROUND OF THE INVENTION

The present invention relates to mobile electronic devices accessories and, more particularly, to a sanitizer/disinfectant distribution apparatus that piggybacks onto mobile electronic devices.

At the time of this writing, over a million people around the globe have contracted COVID-19. It has also been revealed that the novel coronavirus that causes COVID-19 remains for several hours to days on surfaces. Thus, if these surfaces are high-contact surfaces, there is an increased likelihood of perpetuating infections of the novel coronavirus as well as other viruses. It is well known that there are at least hundreds of millions of mobile electronic devices in current use, and their users generally keep them within arm's reach.

Current devices adapted to provide sanitizer or similar viscous products are bulky and not readily available at the point of use. As a result, people do not have such product handy at the time of need.

As can be seen, there is a need for a sanitizer/disinfectant/liquid/gel distribution apparatus that operatively associates with a mobile electronic devices in an easily accessible manner, providing a compact method of keeping sanitizing material with the mobile electronic devices at all time, essentially ensuring its availability. The present invention eliminates the need to carry a separate sanitizer container or other apparatus in a separate manner by having sanitizer delivery apparatus always attached to their mobile electronic device. The present invention is dimensioned and adapted to operatively associate with smart phones, their cases or a combination thereof to easily store and apply refillable sanitizers, perfume or other liquid or gel product.

SUMMARY OF THE INVENTION

In one aspect of the present invention, a piggybacking container for a mobile device includes the following: a replaceable or refillable pouch having a fluidly connected conduit: the pouch being dimensioned to have a pouch surface area generally coextensive with a surface area of said mobile device, and a plurality of attachment points spaced apart along a periphery of the pouch for removably attaching to said mobile device and with ability to use pressure via access point and/or gravity to dispense the contents.

In another aspect of the present invention, a piggybacking container for a mobile device including the following: a pouch having a fluidly connected conduit, the pouch being dimensioned to have a pouch surface area generally coextensive with a surface area of said mobile device, wherein the pouch surface area is defined by a height and a width that each range between an average, but not limited to, 50 to 75 millimeters and 80 to 300 millimeters, respectively; as well as providing clear access to camera lens, a plurality of attachment clips spaced apart along a periphery of the pouch for removably attaching to said mobile device, wherein each attachment clip is pivotable between an operable position for removably attaching to said mobile device and a storage position flush with the pouch surface area: a case for said mobile device, wherein the plurality of attachment points spaced apart are dimensioned for removably attaching to said case, and a fluid/semifluid product in the pouch, wherein the fluid/semifluid product has primarily sanitation or disinfectant properties.

In another aspect of the present invention, a method of operatively associating a sanitizer or disinfectant product to a mobile device includes the following: providing the above-mentioned piggybacking container for a mobile device; moving the plurality of attachment clips to a storage position; and sandwiching said piggybacking container for a mobile device between said mobile device and the case.

These and other features, aspects and advantages of the present invention will become better understood with reference to the following drawings, description and claims.

BRIEF DESCRIPTION OF THE DRAWINGS

FIG. 1 is an exploded perspective view of an exemplary embodiment of the present invention, illustrating operative association with a mobile electronic device;

FIG. 2 is a perspective view of an exemplary embodiment of the present invention, illustrating refilling a pouch 12 with a fluid or viscous product.

FIG. 3 is a perspective view of an exemplary embodiment of the present invention operatively associated with, or "piggybacking" on a mobile electronic device;

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a piggybacking apparatus dimensioned to removably attach to the surface area of a mobile electronic device, such as a smart phone, in a generally coextensive manner. The piggybacking apparatus may provide a pouch for retrievably storing fluid and semifluid product that a user wants handy when they are handling the mobile electronic device. Through a conduit the user may urge the product from the pouch when and where desired. The piggybacking apparatus may also provide attachment points along a periphery thereof for operatively associating with the mobile electronic device in the coextensive manner, or alternatively to a case of the mobile electronic device, or even in between the two.

Referring to FIGS. 1 through 5, the present invention may include a mobile device piggybacking apparatus 10. The piggybacking apparatus 10 may include a flexible pouch 12, which is re-usable and re-fillable. The pouch 12 may be slim or otherwise have a depth of approximately 1 mm or less, while having a height and a width that range between 70 to 75 mm and 150 to 160 mm, respectively; in other words, dimensioned to be generally coextensive with a standard smart phone surface area.

Figure 5:
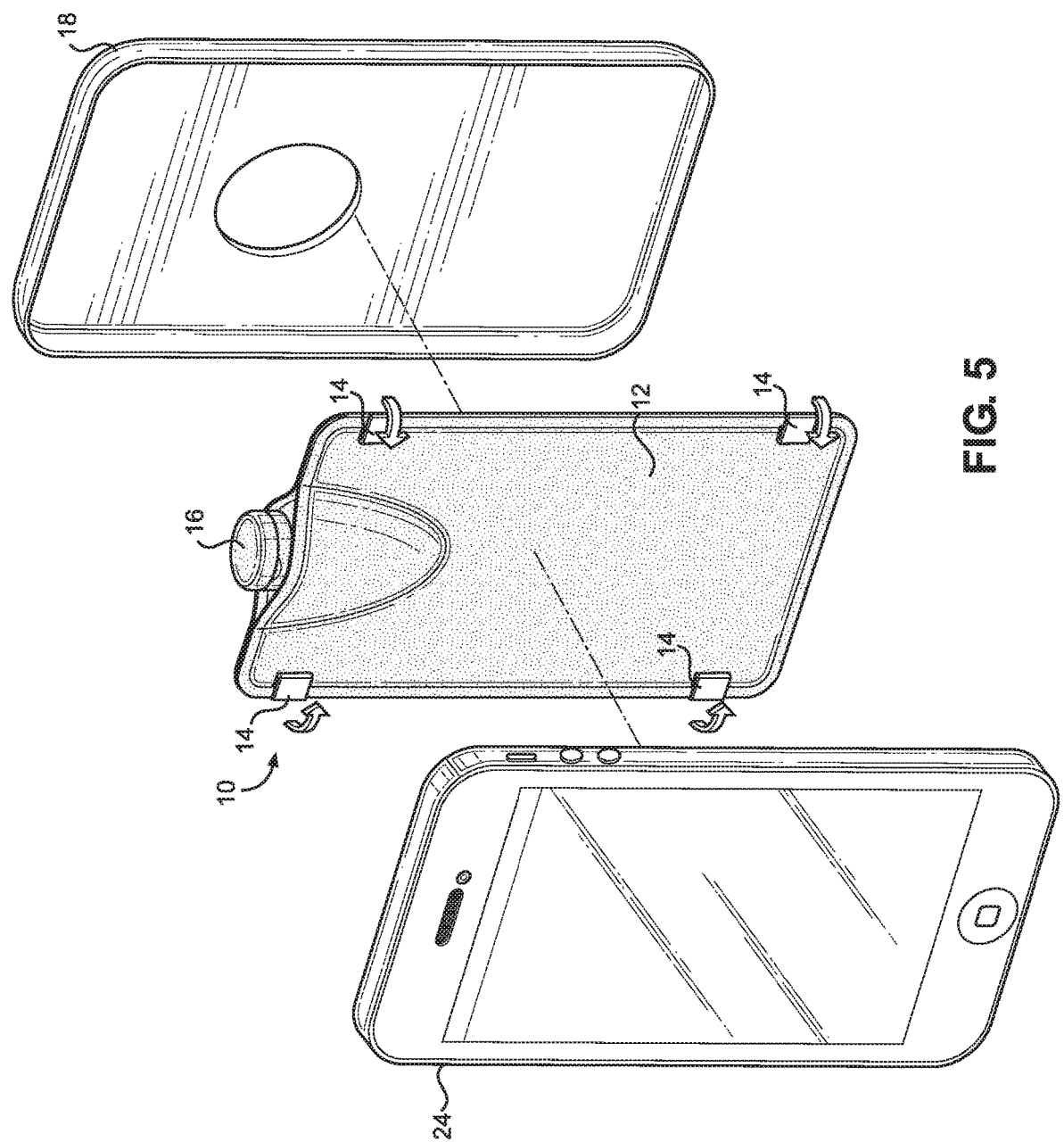
FIG. 5 is an exploded perspective view of an exemplary embodiment of the present invention, illustrating a stored, sandwiched condition between the mobile electronic device and a case thereof.

A plurality of attachment points 14 may be provided spaced apart along a periphery of the pouch 12. The attachment points 14 may be clips, adhesive segments or the like for removably attaching the pouch 12 to a periphery of a smart phone 24 or a case 18 thereof. In certain embodiments, the attachment points 14 may be pivotably attached to the periphery of the pouch 12 so as to move between an operable position (see FIG. 2) for engaging a mobile device 24 and a storage position. In some embodiments, in the storage position, the piggybacking apparatus 10 may be sandwiched between the mobile device 24 and its case 18, as illustrated in FIG. 5.

The pouch 12 provides a conduit 15 fluidly communicating to an interior thereof when the conduit 15 is in an open condition, as illustrated in FIG. 2. The conduit 15 may be threaded spout adapted to be engaged by a cap 16, that can fluidly disconnect said interior and conduit 15, i.e., a closed condition. The piggybacking apparatus 10 retrievably stores product 20 therein, enables a user 22 to squirt or squeeze out the product 20 by applying pressure to an exterior of the pouch 12. The product 20 may be fluid, gel, oil, ointment or semifluid product and/or gel that has sanitization and/or disinfection properties, or the like.

Figure 4:
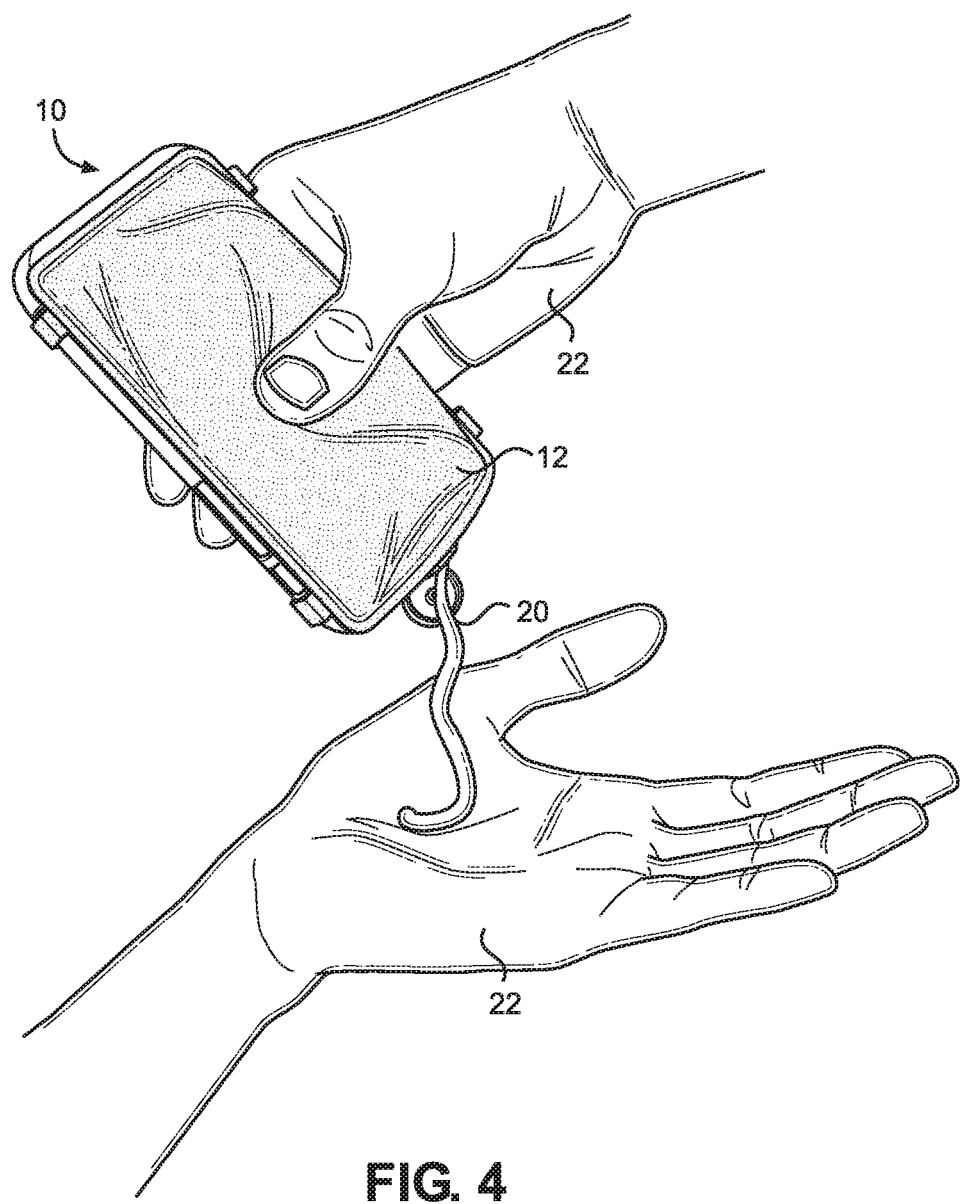
FIG. 4 is a perspective view of an exemplary embodiment of the present invention, shown in use.

A method of using the present invention may include the following. The piggybacking apparatus 10 disclosed above may be provided. A user 22 would be able to have sanitizing, disinfecting, and other lubricating product 20 at their fingertips at all time they had their mobile device handy. The user 22 could fill the pouch 12 with the product 20 for subsequent use and seal the cap 16 placing the conduit 15 in a closed condition. Through the attachment points 14 a user could removably attach the pouch 12 to a rear surface of their mobile device 24 so that the pouch 12 is substantially coextensive thereto. Immediately after the user 22 touches something that is dirty or possibly germ-covered, they can move the cap 16 to an open condition and urge the product 20 onto a surface, such as their hands, as illustrated in FIG. 4. Then the user may replace the cap 16, forming the closed position. By having the present invention attached to the mobile device 24, the user 22 will always have the cleaning product 20 nearby. The present invention will allow the user to refill the pouch 12, as illustrated in FIG. 2.

Additionally, the present invention could be expanded to attach to key chains, and other small personal materials.

It should be understood, of course, that the foregoing relates to exemplary embodiments of the invention and that modifications may be made without departing from the spirit and scope of the invention as set forth in the following claims.

What is claimed is:

1. A piggybacking container for a mobile device, comprising: a pouch having a fluidly connected conduit;
   the pouch being dimensioned to have a pouch surface area generally coextensive with a surface area of said mobile device; and
   a plurality of clips spaced apart along a periphery of the pouch for removably attaching to said mobile device, wherein each clip is pivotable between an operable position for removably attaching to said mobile device and a storage position flush with the pouch surface area.

2. The piggybacking container for a mobile device of claim 1, further comprising:
   a fluid/semifluid product in the pouch.

3. The piggybacking container for a mobile device of claim 2, wherein the fluid/semifluid product has primarily sanitation or disinfectant properties.

4. The piggybacking container for a mobile device of claim 1, wherein the pouch surface area is defined by a height and a width that each range between 70 to 75 millimeters and 150 to 160 millimeters, respectively.

5. The piggybacking container for a mobile device of claim 1, further comprising a case for said mobile device, wherein the plurality of clips spaced apart are dimensioned for removably attaching to said case.

6. A piggybacking container for a mobile device, comprising:
   a pouch having a fluidly connected conduit;
   the pouch being dimensioned to have a pouch surface area generally coextensive with a surface area of said mobile device, wherein the pouch surface area is defined by a height and a width that each range between 70 to 75 millimeters and 150 to 160 millimeters, respectively;
   a plurality of attachment clips spaced apart along a periphery of the pouch for removably attaching to said mobile device, wherein each attachment clip is pivotable between an operable position for removably attaching to said mobile device and a storage position flush with the pouch surface area; and
   a case for said mobile device, wherein the plurality of clips spaced apart are dimensioned for removably attaching to said case.

7. The piggybacking container for a mobile device of claim 6, further comprising a fluid/semifluid product in the pouch, wherein the fluid/semifluid product has primarily sanitation or disinfectant properties.

8. A method of operatively associating a sanitizer or disinfectant product to a mobile device, comprising:
   providing the piggybacking container for a mobile device of claim 7;
   moving the plurality of attachment clips to a storage position; and
   sandwiching said piggybacking container for a mobile device between said mobile device and the case.

* * * * *